United States Patent [19]

Snyder

[11] Patent Number: 5,207,651
[45] Date of Patent: May 4, 1993

[54] TRACTION TUBE HOLDER AND METHOD

[76] Inventor: Nancy Snyder, 910 Old Hills Rd., Boston, Pa. 15135

[21] Appl. No.: 797,042

[22] Filed: Nov. 25, 1991

[51] Int. Cl.$^5$ ............................................. A61M 5/32
[52] U.S. Cl. ..................................... 604/174; 604/178
[58] Field of Search ............... 604/174, 177, 178, 179, 604/180; 128/DIG. 26

[56] References Cited

U.S. PATENT DOCUMENTS

| | | | |
|---|---|---|---|
| 4,516,968 | 5/1985 | Marshall et al. | 604/174 |
| 4,699,616 | 10/1987 | Nowak et al. | 604/180 |
| 4,784,647 | 11/1988 | Gross | 604/178 |
| 4,874,380 | 10/1989 | Hesketh | 604/180 |
| 4,915,694 | 4/1990 | Yamamoto et al. | 604/180 |
| 5,026,352 | 6/1991 | Anderson | 604/180 |
| 5,073,170 | 12/1991 | Schneider | 128/DIG. 26 |

*Primary Examiner*—Cary E. O'Connor
*Attorney, Agent, or Firm*—Gary P. Topolosky

[57] ABSTRACT

There is provided an improvement to a device for slidably mounting a tube against an orifice of a medical patient, the device including a polygonal section of sponge foam, a bore through this foam and a slot for enabling the polygonal section of foam to be slid over and onto a tube. The improvement comprises a rigid backing plate that fixedly attaches to the sponge foam in an area apart from, and preferably opposite, the surface of the sponge foam section in contact with the patient's orifice. This backing plate has a bore and slot corresponding to those in the sponge foam section. With this improvement, such mounting devices may be placed in more permanent traction against the patient's nose, mouth or other orifice. A further improvement includes a gauge for varying the amount of substantially permanent traction placed on a medical tube with this device. There is also disclosed a method for supplying variable amounts of substantially permanent traction to a medical tube with the holder of this invention.

18 Claims, 2 Drawing Sheets

TRACTION TUBE HOLDER AND METHOD

BACKGROUND OF THE INVENTION

1. Field of the Invention

This invention relates to the general field of medical devices. The invention particularly relates to a device and method for holding medical tubes, balloons and the like (hereinafter "implements") in place adjacent the mouth, nose or other orifice of a medical patient. The invention is best suited for keeping such implements in place with substantially permanent traction. The invention provides novel means for holding such implements in position while allowing for adjustment of the amount of traction to be placed thereon.

2. Technology Review

Numerous medical tube holders have been designed and patented over the past forty years. Very few allege to possess any traction-imparting abilities, however. U.S. Pat. No. 2,669,231 claims an anchor construction for removably retaining flexible tubes without constricting said tubes. The anchor construction consists of a sponge rubber, yieldable pad adhesively mounted to a woven cotton strip. The outer edges of this strip are provided with metal eyelets for stringing a fastening line therethrough.

In U.S. Pat. No. 2,898,917, the catheter or drainage tube holder that is disclosed consists of a one-piece, rubber latex retention disk secured to the patient's skin with a surgical adhesive. The disk portion of this holder conforms to the surface of the body being treated.

U.S. Pat. No. 3,046,988 claims an improved esophageal, nasogastric tube similar to the type of balloon/catheter systems most commonly employed with the present invention. A part of this prior art tube comprises a nasal cuff preferably constructed of non-toxic sponge foam. The cuff includes a bore that extends completely through, said bore connecting to an outer edge of the cuff via slot 60 in FIG. 5. Although this cuff alleges to provide some traction, it is this inventor's experience that the traction provided by such a spongelike cuff is inconsistent, unpredictable and rather short-lived. As these cuffs absorb moisture from the patient's nose or mouth, they loosen their grip on the tubes passing therethrough.

The nasal tube holder of U.S. Pat. No. 3,046,989 consists of a thin, ductile sheet of aluminum to which is adhesively mounted a plastic-coated paper or other protective sheath for sanitation, storage and handling purposes. The tube holding portion of said invention comprises a tab from the aluminum sheet for wrapping about the patient's nasal tube.

U.S. Pat. No. 3,286,713 addresses surgical dressing made from folded sheets of absorbent material, said sheets having a pair of spaced apart apertures through which a tubular object passes. This dressing allegedly frictionally engages with the tube by gripping thereon to avoid any need for surgical adhesives.

An endotracheal tube holder is shown in U.S. Pat. No. 3,946,742. This tube holder comprises an opensided retainer 24 fixedly mounted to the upper end of an arm pivotally pinned to a plastic strap 14 for securing about the neck of a patient. U.S. Pat. No. 3,976,080 claims an alternate tube holder, also strapped about the patient's head using slots 28, said tube holder including a frame-mounted projection upon which the tube rests, and a pair of opposing tabs for serving as stop lugs.

In the nasogastric tube holder of U.S. Pat. No. 4,120,304, a clamp portion 4 comprises a rigid, generally circular disk having a hole and slot cut therethrough. Although this clamp is necessary to the remainder of this prior art tube holder as shown, it does not contact with the patient's nose and cannot provide any traction to the tube being held in place therewith.

U.S. Pat. No. 4,142,527 shows yet another variation of endotracheal tube holder, which variation employs an adhesive-backed strip portion for securing a tube holding portion to the patient's nose. The tube holding portion includes a section of Velcro (or hook and eye interlocking) tape.

In U.S. Pat. No. 4,261,363, there is claimed a retention clip for body fluid drains. The upper portion of this clip is longitudinally slotted for sideways insertion of a drain there-through. The base portion of this clip may be taped or otherwise secured to the patient's body. Preferred embodiments of this clip are made from semi-resilient material such as polyvinyl chloride.

The medical tube holder of U.S. Pat. No. 4,336,806 comprises a generally rectangular backing strip made from a porous foam plastic material. A plurality of magnets are laminated onto the inner surface of this backing strip for securing to one another about the medical tube being held in place when the backing strip is folded onto itself.

U.S. Pat. No. 4,392,857 claims a tube clamp whose length-wise base lies disposed along a section of tube with a U-shaped strap retainer fixed to this base, a strap fixed to one end of the base, at least one side of said strap and one arm of the retainer having complementally-formed triangular slots. A lower side of this clamp includes pressure sensitive adhesive for securing to a patient's skin.

The tube retaining device of U.S. Pat. No. 4,480,639 comprises a flexible strap with first clamp means for positioning beneath a patient's nose, and second clamp means near one end of the strap for holding the tube in a fixed position adjacent the patient.

There is claimed an endotracheal tube holder in U.S. Pat. No. 4,683,882. This tube holder includes a base for supporting an adhesive strap that secures the holder about the mouth of a patient. An adjustable clamp releasably secures a tube through a central opening in this base, said clamp being either a gate-type, C-clamp or notched strap type.

U.S. Pat. No. 4,520,813 shows yet another form of endotracheal tube holder within a pair of identical, curved plate-like hooking members, each with a dogleg opening, interconnect about the tube before being attached about a patient's neck or face with Velcro bands.

In U.S. Pat. No. 4,606,735, a detachable medical tube holder is described. This tube holder is formed from a flexible plastic strip having upstanding end wings, each of which is provided with a pair of snap-in keyhole slots in axial alignment with one another. It is secured to a patient's skin using male and female Velcro tape fasteners.

The medical tube holder of U.S. Pat. No. 4,622,034 consists of a multi-apertured foam strip for wrapping about the head of a patient and inserting a tracheal or nosogastric tube through any two aligned holes on opposite ends of the strip. An alternate embodiment employs Velcro fastening means.

U.S. Pat. No. 4,844,061 shows a medical tube holder that includes an elongated strip of resilient fabric with porous foam bonded thereto. At one end of this strip, an aperture fits over a portion of the medical tube extending outwardly from the patient's mouth. A thin piece of adhesive wraps about the tube before securing to itself to form a ring about the tube.

Still other tube holders are set forth in U.S. Pat. Nos. 4,867,154, 4,906,234, 4,959,055, 5,009,227, 5,017,188, 5,027,188, 5,026,352 and 5,031,775.

SUMMARY OF THE INVENTION

It is a principal objective of the present invention to provide a medical tube traction device which doesn't require sophisticated or complicated means for holding a medical implement adjacent a patient's mouth, nose or other orifice. It is another objective to provide a traction tube device that avoids the use of pulleys, helmets or other currently known means for holding such implements in place about the orifice of a patient. It is yet another objective to provide a tube holding/mounting device with means for varying the amount of traction to be placed on such medical implements.

It is another principal objective of this invention to provide a tube holding device for use in treating patients suffering from esophageal varacies and other liver-disease associated ailments. It is yet another objective to provide traction tube holders for the catheters used to treat genito-urinary or tamponade nasal bleeding. It is another objective to provide a device for placing variable amounts of traction on the tubes and/or balloons used to treat patients suffering from a variety of internal bleeding disorders, thereby enabling such patients to avoid going into shock.

It is another main objective to provide a method for placing various amounts of traction (or tension) on the tubes used to treat certain medical conditions. It is still another objective to provide an uncomplicated tube holding device which can be made into various sizes. This device preferably contains rounded edges for preventing injury and providing comfort to a medical patient during use. It is yet another objective to provide this device with a foam, spongelike cushion for contacting the patient's body while not causing any irritation thereto. Said cushion would adsorb body fluids that may tend to leak or drain from the patient's orifice.

These and further objectives of the present invention are met by providing an improvement to a device for slidably mounting a tube against an orifice of a medical patient, said device including a polygonal section of sponge foam, a bore through this foam and a slot for enabling the polygonal foam section to be slid over and onto a tube. The improvement comprises a rigid backing plate that fixedly attaches to the sponge foam in an area apart from, and preferably opposite, that area of the sponge foam section in contact with the patient's orifice. This backing plate has a bore and slot corresponding to those in the sponge foam section. With this improvement, mounting devices of the present invention may be placed in more permanent traction against the patient's nose, mouth or other draining orifice. A still further improvement comprises means for varying the level or amount of permanent traction to be placed on a medical tube with devices of this sort. There is further disclosed a method for supplying variable amounts of substantially permanent traction to a medical tube extending from the orifice of a patient.

BRIEF DESCRIPTION OF THE DRAWINGS

Further features, other objectives and advantages of the present invention will be made clearer from the following detailed description of preferred embodiments made with reference to the drawings in which.

DETAILED DESCRIPTION OF THE PREFERRED EMBODIMENTS

Figure 1:
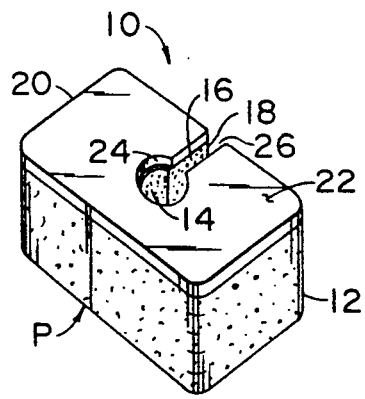
FIG. 1 is a perspective view of one embodiment of the present invention.
Figure 2:
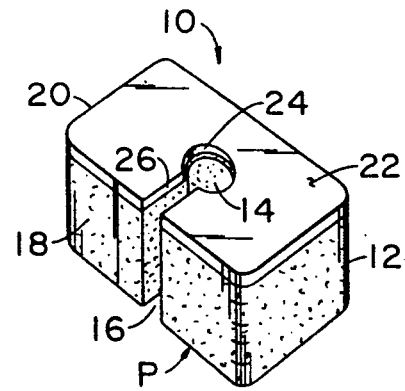
FIG. 2 is a perspective view of the reverse side of the device depicted in FIG. 1.

Referring now to FIGS. 1 and 2, there is shown an improved device according to the invention. The device, generally 10, includes a polygonal section of sponge foam 12, having a bore 14 which is preferably centrally located to extend completely through sponge section 12. Although the sponge foam of FIGS. 1 and 2 is generally rectangular, it is to be understood that section 12 may be cubical, hexagonal, octagonal, or assume any other desired, three-dimensional shape. A slot 16 connects bore 14 to a lateral edge 18 of sponge foam section 12, though there is no functional significance as to which edge of the foam section slot 16 extends. The slot is merely intended to enable the sponge from section to be slid over and onto a medical tube for holding this device against, and preferably adjacent, the orifice of a medical patient.

An improvement to the foregoing device comprises a rigid backing plate 20 with an inside surface (not shown) that is fixedly attached to an area of the sponge foam section 12 apart from, and preferably opposite, that area of the foam section in contact with the patient's orifice. In FIGS. 1 through 4, the patient-contacting side of the device is identified by arrow P. On a preferred basis, rigid plate 20 is glued or otherwise adhesively secured to sponge foam section 12. It is to be understood, however, that other securing means, such as snaps, fasteners, or even corresponding sections of hook and eye (or Velcro) tape may be substituted therefor.

Rigid plate 20 is preferably made from a non-toxic, yet firm plastic resin though it is to be understood that said member could also be made from metal, a rigid paper product, reinforced fabric(s) or a composite blend. In any event, rigid plate 20 includes an outer surface 22 opposite from that surface of the sponge foam section in contact with the patient's nose, mouth, other wound (incision). A bore 24 and slot 26 extend through rigid plate 20 in roughly the same position that bore 14 and slot 16 extend through foam section 12. On a preferred basis, foam section 12 and rigid plate 20 are of substantially similar length and width. However, it is most preferred that foam section bore 14 be of a slightly smaller diameter than plate bore 24 to provide a snug, slightly tighter fit around the medical tube extending through this device. It is also preferred that most every edge to both the foam section and rigid plate be rounded for providing greater patient comfort and reduced risk of injury.

The first embodiment of this invention is available in a variety of shapes and sizes for use against a plurality of different patient orifices. Foam section 12 may be planar for positioning adjacent a patient's nose or mouth. It may also be curved, angled or slightly wedge-shaped to meet different patient-contacting needs. Opposite sides to this device are preferably planar though it is to be understood that curved, arched, angled, or even multi-sectional rigid plates may be combined with most any shape of foam section.

Figure 4:
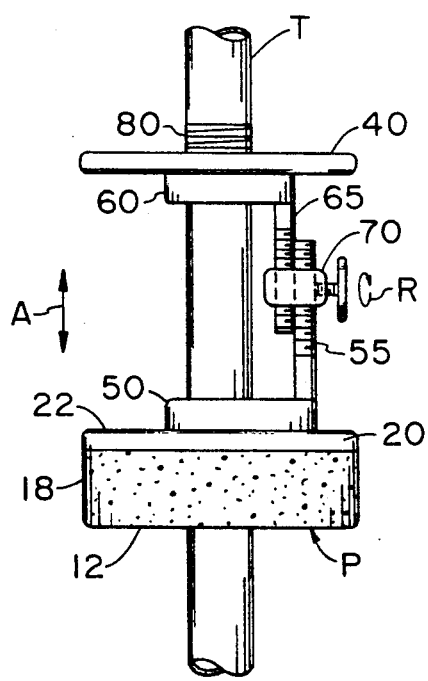
FIG. 4 is an enlarged side view of the device depicted in FIG. 3.
Figure 3:
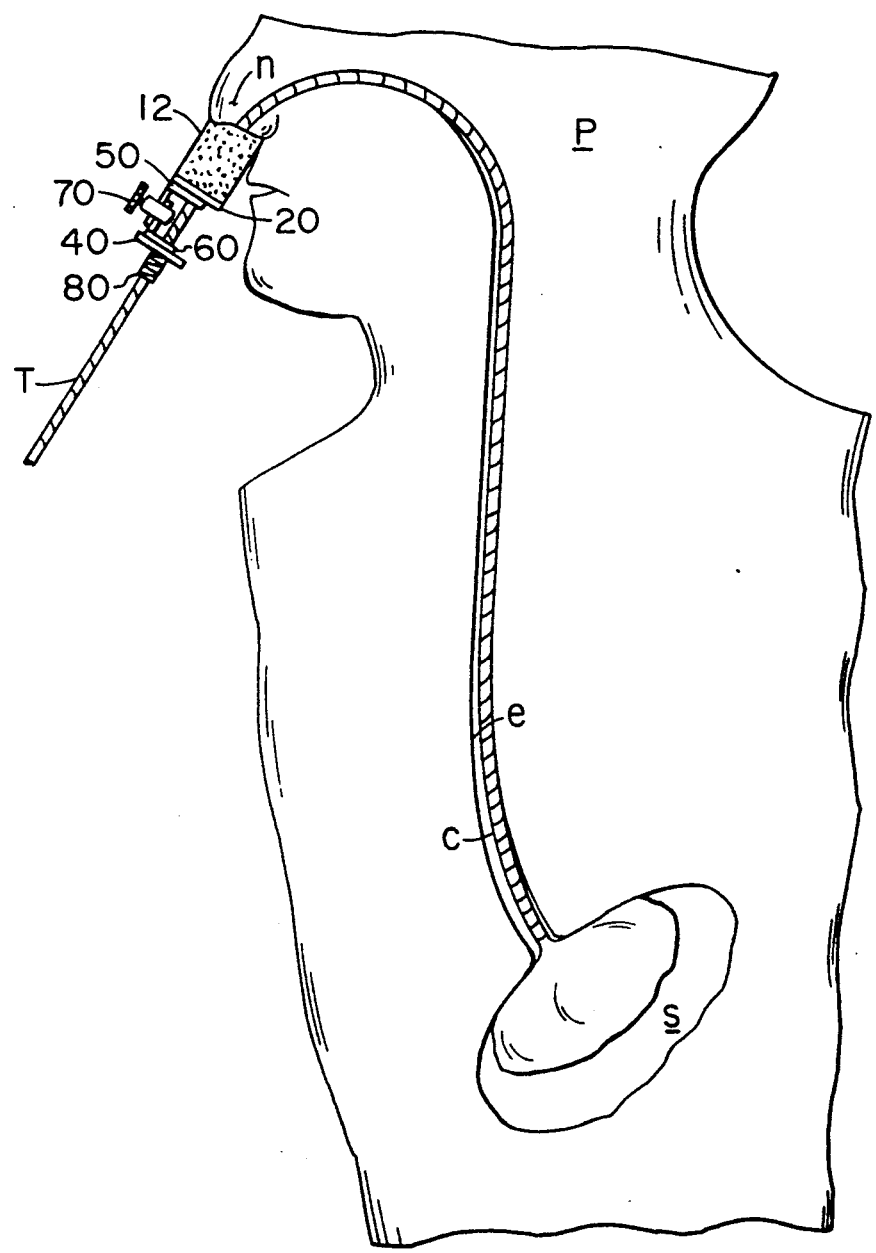
FIG. 3 is a side elevational view of another embodiment of the invention installed adjacent the mouth of a medical patient.

Referring now to FIGS. 3 and 4, there is shown a second preferred embodiment which includes means for adjusting the amount of substantially permanent traction (or tension) placed on the medical tube passing through the present invention. One such traction adjusting means comprises a clamp 30 whose distance along tube T and apart from rigid plate 20 varies, preferably parallel to that of the tube passing therethrough, or in the direction of arrow A in FIG. 3.

On a preferred basis, the traction adjustment means of this second embodiment includes a second rigid plate 40 spaced outwardly from and substantially parallel to the first rigid plate 20. Like this first plate, second plate 40 has a bore 44 and slot 46 that connects bore 44 to a lateral edge 48 of second plate 40.

One clamping means for varying the distance between first plate 20 and second plate 40 comprises a first clamping member 50 positioned about tube T adjacent first plate 20. A first threaded arm 55, extends upwardly and outwardly from first clamping member 50 towards second plate 40. A second clamping member 60, positioned adjacent second plate 40, includes its own outwardly extending arm 65 threaded to correspondingly contact or engage with arm 55 of the first clamping member. A dial-type gauge 70 secures the two arms of the respective clamping members together. Gauge 70 preferably rotates in a clockwise direction, as identified by arrow R in the Figures, to vary the amount of traction-like pressure (or tension) that may be asserted on a tube extending therethrough. On a more preferred basis, gauge 70 is calibrated with dashes and/or numerals for designating the various levels of pressure, such as 1, 2 or 3 pounds (lbs.) of traction, to be placed on a tube T with the present device.

For a greater control of the traction asserted on tube T by device 10, it is preferred that second plate 40 be substantially secured in a fixed position from behind but somewhere along the length of tube T. There are several ways to accomplish this result. One representative means includes positioning a section of hook and eye (or Velcro) tape 80 about itself and tube T at a point farthest from the patient's orifice. Still other means for securing second plate 40 about tube T, such as common surgical tape, may be substituted for Velcro section 80.

Figure 5:
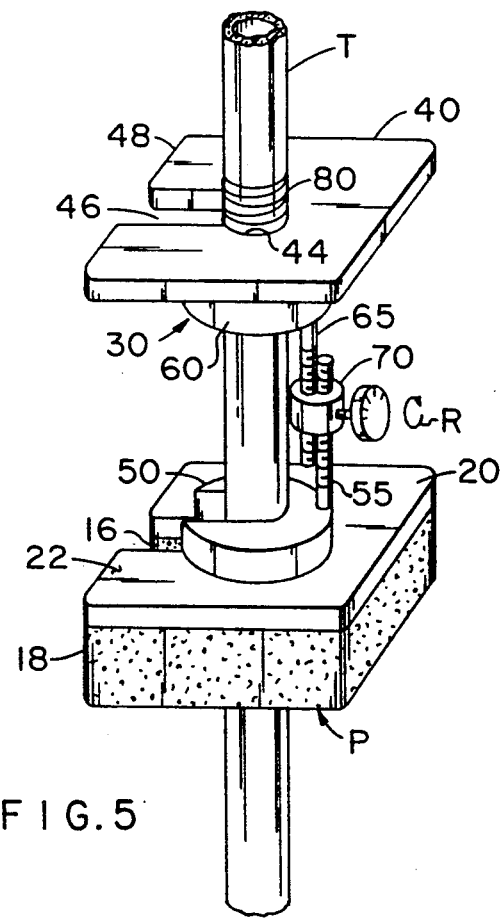
FIG. 5 is a perspective view of the device depicted in FIG. 4.

FIG. 5 shows one method for supplying variable amounts of substantially permanent traction (as defined earlier) to a medical tube with the holder/device shown in FIGS. 3 and 4. The invention can be used on patients suffering from a plurality of disorders. It is especially suitable for treating internal bleeding complications thereby preventing such patients from going into shock due to excessive blood loss. This device and method may be used on patients suffering from esophageal varacies. This tube holder may also be used in combination with: a Minnesota (or Sangsten blakemore) tube; or with a Foley-type of catheter for treating genito-urinary bleeding.

In FIG. 5, patient P is silhouetted for showing his esophageal passageway e leading to stomach area s. A balloon-type catheter c extends through this patient's nose n and esophagus before passing through the gastroesophageal junction and entering the stomach. For some liver patients, it is critical that substantially permanent traction be used to keep tube T against the stomach's uppermost lining. The device of this invention helps considerably in this regard. Such an improved tube holder may be installed easily about the patient's orifice to be treated with medical tube T. Clamping means are then used to enable rotation of dial 70 until a proper spacing is achieved between the two rigid plates 20 and 40. In some instances, it may be necessary to readjust this clamping means for later increasing or lessening the distance between plates 20 and 40 thereby raising or lowering the amount of traction being asserted on tube T.

Having described the presently preferred embodiments, it is to be understood that the invention may be otherwise embodied within the scope of the appended claims.

What is claimed is:

1. In a device for slidably mounting a tube against an orifice of a medical patient, said device including a polygonal section of sponge foam, a bore extending through the sponge foam section, and a slot for enabling the sponge foam to be slid over and onto the tube, an improvement which comprises a rigid backing plate fixedly attached to the sponge foam section in an area of the device apart from where the sponge foam section contacts with the patient's orifice, said backing plate having a bore corresponding to the position of the bore in the sponge foam section and a slot corresponding to the position of the slot in the sponge foam section, the bore in said backing plate being sized to fit tightly against the tube extending through the bore's entire length and the bore through the sponge foam section being sized slightly smaller than the backing plate bore, said backing plate enabling the device to be placed in substantially permanent traction against the patient's orifice.

2. The improvement of claim 1 wherein the tube is an esophageal tube.

3. The improvement of claim 1 wherein the backing plate is made from non-toxic plastic.

4. The improvement of claim 1 wherein the backing plate is fixedly attached to at least one surface of the sponge foam section opposite that area of the sponge foam section in contact with the patient's orifice.

5. The improvement of claim 1 wherein the device slidably mounts adjacent the patient's nose or mouth.

6. The improvement of claim 1 wherein the backing plate and surface of sponge foam section to which the backing plate is attached are of substantially similar length and width.

7. The improvement of claim 1 which further comprises means for varying the amount of substantially permanent traction placed on the tube.

8. The improvement of claim 7 wherein the traction varying means includes at least one clamp whose distance along the tube and apart from the backing plate varies in a direction parallel to the tube.

9. A device for mounting a medical tube in substantially permanent traction against an orifice of a medical patient, said device comprising:
 (a) a polygonal section of sponge foam having: a bore extending therethrough; and a slot for connecting the bore to a lateral edge of the sponge foam section thereby enabling the sponge foam section to be slid over the tube and against the patient's orifice;
 (b) a first rigid plate fixedly attached to a surface of the sponge foam section opposite that portion of the sponge foam section in contact with the patient's orifice, said first rigid plate having a bore and slot corresponding to the position of the bore and slot in the sponge foam section; and
(c) means for adjusting the amount of substantially permanent traction placed on the tube passing through said device, said traction adjusting means including:
(i) a second rigid plate spaced outwardly from and substantially parallel to the first plate and sponge foam section against the patient's orifice, said second plate having a bore and slot for connecting the bore to a lateral edge of the second plate; and
(ii) clamping means for varying the distance between the first and second rigid plates.

10. The device of claim 9 wherein the traction adjusting means includes at least one clamp whose distance along the tube and apart from the first rigid plate varies in a direction parallel to the tube.

11. The device of claim 9 wherein the clamping means includes:
(a) a first clamping member positioned about the medical tube adjacent the first rigid plate, said first clamping member having a threaded arm that extends upwardly toward the second plate;
(b) a second clamping member positioned about the medical tube adjacent the second rigid plate, said second clamping member having an arm threaded to correspondingly contact the arm of the first clamping member, said second clamping member arm extending downwardly toward the first rigid plate; and
(c) means for adjustably securing the first clamping member arm to the second clamping member arm.

12. The device of claim 11 wherein said first clamping member is integrally formed with or permanently secured to the first rigid plate.

13. The device of claim 11 wherein said second clamping member is integrally formed with or permanently secured to the second rigid plate.

14. The device of claim 11 which further includes:
(d) means for substantially permanently securing the second rigid plate about the medical tube.

15. The device of claim 14 wherein the second plate securing means includes a section of Velcro tape for securing about the tube on a side of the second plate opposite the second clamping member.

16. A method for supplying variable amounts of substantially permanent traction to a medical tube extending from an orifice of a medical patient, said method comprising:
(a) providing a device comprising:
(i) a polygonal section of sponge foam having a central bore and a slot for connecting the bore to a lateral edge of the sponge foam section;
(ii) a first rigid plate fixedly attached to a surface of the sponge foam section opposite the surface of said section in contact with the patient's orifice, said first plate having a bore and slot corresponding to the position of the bore and slot in said sponge foam section;
(iii) a second rigid plate spaced outwardly from and substantially parallel to the first plate; and
(iv) clamping means for varying the distance between the first and second rigid plates;
(b) installing the device about the medical tube adjacent the patient's orifice; and
(c) adjusting the clamping means until the two rigid plates are spaced apart a proper distance to impose the desired level of traction on said tube.

17. The method of claim 16 wherein said device further includes Velcro tape for securing the second plate about the tube from a side of the second plate opposite the clamping means.

18. The method of claim 16 which further includes:
(d) readjusting the clamping means to increase or lessen the distance between the first and second rigid plates.

* * * * *